(12) United States Patent
Reeder, Jr. et al.

(10) Patent No.: US 7,981,116 B2
(45) Date of Patent: Jul. 19, 2011

(54) RADIOLUCENT SCREWDRIVER FOR ORTHOPEDIC SURGERY

(75) Inventors: Ralph F. Reeder, Jr., Dakota Dunes, SD (US); Mahmoud Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 1043 days.

(21) Appl. No.: 11/753,632

(22) Filed: May 25, 2007

(65) Prior Publication Data

US 2008/0294173 A1 Nov. 27, 2008

(51) Int. Cl.
*A61B 17/58* (2006.01)
(52) U.S. Cl. .................................................. 606/104
(58) Field of Classification Search ............ 606/99, 606/104, 912; 81/177.5
See application file for complete search history.

(56) References Cited

U.S. PATENT DOCUMENTS

| | | | | |
|---|---|---|---|---|
| 2,248,054 A * | 7/1941 | Becker | | 81/457 |
| 2,678,578 A * | 5/1954 | Bonanno | | 81/436 |
| 3,988,180 A * | 10/1976 | Bouvaist | | 148/701 |
| 5,059,193 A * | 10/1991 | Kuslich | | 606/247 |
| 5,236,431 A * | 8/1993 | Gogolewski et al. | | 606/139 |
| 5,571,103 A * | 11/1996 | Bailey | | 606/62 |
| 5,951,556 A * | 9/1999 | Faccioli et al. | | 606/65 |
| 5,980,455 A * | 11/1999 | Daniel et al. | | 600/235 |
| 6,436,100 B1 * | 8/2002 | Berger | | 606/916 |
| 2001/0004610 A1 * | 6/2001 | Casutt | | 464/33 |
| 2003/0069600 A1 * | 4/2003 | Falahee | | 606/205 |
| 2004/0049251 A1 * | 3/2004 | Knowlton | | 607/101 |
| 2004/0167519 A1 * | 8/2004 | Weiner et al. | | 606/60 |
| 2004/0220567 A1 * | 11/2004 | Eisermann et al. | | 606/61 |
| 2004/0243146 A1 * | 12/2004 | Chesbrough et al. | | 606/130 |
| 2006/0074445 A1 * | 4/2006 | Gerber et al. | | 606/191 |
| 2006/0201287 A1 * | 9/2006 | Abdelgany | | 81/177.5 |

* cited by examiner

*Primary Examiner* — Thomas C Barrett
*Assistant Examiner* — Christian Sevilla
(74) *Attorney, Agent, or Firm* — Rahman LLC (57) ABSTRACT

A surgical tool for inserting a surgical implant in a body and a method of performing a surgical procedure, wherein the tool is composed of materials consisting essentially of radiolucent materials. In one embodiment the radiolucent materials comprise plastic. In another embodiment the radiolucent materials comprise carbon fibers. In still another embodiment the radiolucent materials comprise thin aluminum. The tool has a torque capacity of at least 6 Nm.

14 Claims, 9 Drawing Sheets

RADIOLUCENT SCREWDRIVER FOR ORTHOPEDIC SURGERY

BACKGROUND

1. Technical Field

The embodiments herein generally relate to medical devices, and, more particularly, to screwdrivers used during orthopedic surgeries.

2. Description of the Related Art

During minimally invasive surgery, scoliosis surgery, or deformity surgery, a surgeon will usually utilize an X-ray device to determine the location and/or direction of insertion of an implant such as a screw or a nail into bone. Without the guidance of the X-ray imaging machines, this can be a dangerous endeavor due to the lack of direct sight, and abnormal anatomy where all or some of the anatomical norms are not applicable. The most common surgical imaging machine in use today is an X-ray emitting device sometimes referred to as a C-arm.

X-rays are similar to light in that they comprise electromagnetic waves, but they are more energetic so they can penetrate many materials to varying degrees. When the X-rays hit an imaging film, they expose the film just as light would. Since bone, fat, muscle, tumors, and other masses all absorb X-rays at different levels, the image on the film lets one see different (distinct) structures inside the body because of the different levels of exposure on the film. Implants made of metallic materials can then appear clearly during and after insertion.

Currently, all implant inserters are also made of metallic components that block the X-rays from showing the direction and location of the implants during implantation. Some surgeons resort to removing the standard metallic inserters prematurely to allow for imaging and then trying to reconnect in the surgical field. This process can be a time consuming and frustrating activity for the surgeon. Accordingly, there remains a need for a new tool to allow surgeons to clearly view implant devices during surgical procedures without having to remove the inserter prior to the end of the surgical procedure.

SUMMARY

In view of the foregoing, an embodiment provides a surgical tool for inserting a surgical implant in a body, wherein the tool is composed of materials consisting of radiolucent materials. In one embodiment the radiolucent materials comprise plastic. In another embodiment the radiolucent materials comprise carbon fibers. In still another embodiment the radiolucent materials comprise thin aluminum. Preferably, the tool has a torque capacity of at least 6 Nm.

Another embodiment provides a surgical inserter comprising a body portion comprising radiolucent materials; and a tip portion operatively connected to the body portion. In one embodiment the tip portion comprises radiolucent materials. In another embodiment the tip portion comprises steel. Preferably, the tip portion is adapted to engage a surgical implant. Moreover, the radiolucent materials may comprise any of plastic, carbon fibers, and aluminum. Furthermore, the tip portion preferably comprises a torque capacity of at least 6 Nm. Additionally, the body portion may be dimensioned and configured as a screwdriver.

Another embodiment provides a method of performing a surgical procedure, wherein the method comprises providing an implant inserter comprising radiolucent materials; engaging a surgical implant with the radiolucent implant inserter; inserting the surgical implant in a body with the radiolucent implant inserter; and taking X-ray photography of the surgical implant with the radiolucent implant inserter operatively connected thereto, wherein the radiolucent implant inserter is at least partially within the body during the taking of the X-ray photography. Preferably, the implant inserter comprises a body portion comprising the radiolucent materials; and a tip portion operatively connected to the tip portion. In one embodiment the tip portion comprises radiolucent materials. In another embodiment the tip portion comprises steel. Preferably, the radiolucent materials comprise any of plastic, carbon fibers, and thin aluminum. Furthermore, the implant inserter preferably comprises a torque capacity of at least 6 Nm. Also, the implant inserter may comprise a screwdriver. Additionally, the method may further comprise disposing the implant inserter after use.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIGS. 6(A) through 6(D) illustrate various views of the first arm of the attachment mechanism of FIGS. 5(A) through 5(D) according to the embodiments herein;

FIGS. 7(A) through 7(D) illustrate various views of the second arm of the attachment mechanism of FIGS. 5(A) through 5(D) according to the embodiments herein;

FIGS. 8(A) through 8(D) illustrate various views of the locking sleeve of the attachment mechanism of FIGS. 5(A) through 5(D) according to the embodiments herein;

DETAILED DESCRIPTION OF PREFERRED EMBODIMENTS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new tool to allow surgeons to clearly view implant devices during surgical procedures without having to remove the inserter prior to the end of the surgical procedure. The embodiments herein achieve this by providing a radiolucent screwdriver that has a minimal or non existent X-ray footprint while driving the orthopedic implant such as a screw or a nail to its destination under imaging thereby helping the surgeon avoid critical anatomy such as blood vessels and nerve tissue and saving valuable operating room time. Referring now to the drawings, and more particularly to FIGS. 1 through 10, where similar reference characters denote corresponding features consistently throughout the figures, there are shown preferred embodiments.

Figure 1:
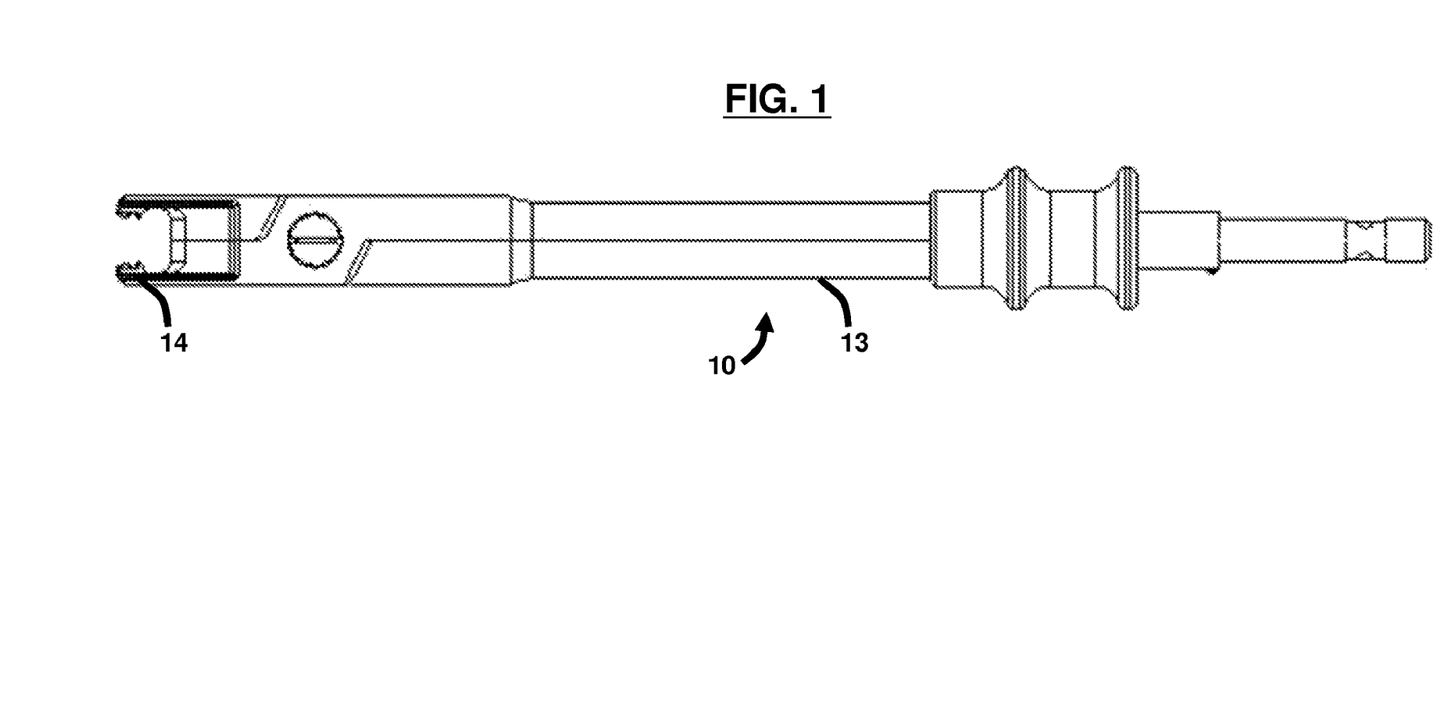
FIG. 1 illustrates a schematic diagram of a radiolucent inserter according to a first embodiment herein.

FIG. 1 illustrates a radiolucent implant inserter 10 used to insert an orthopedic implant (not shown). The inserter 10 may be configured similar to the screwdriver described in U.S. patent application Ser. No. 11/063,452, filed on Feb. 23, 2005, the complete disclosure of which in its entirety is herein incorporated by reference. The body portion 13 and tip portion 14 of the inserter 10 is made exclusively of radiolucent materials that do not block or interfere with intermittent or constant X-ray monitoring therefore eliminating the need to (a) disengage the inserter 10 from the implant to determine the direction/location of the implant, and (b) re-engage the inserter 10 to the implant to continue insertion.

The inserter 10 is applied during surgery to allow a surgeon to utilize constant or occasional X-ray imaging while implanting implants with the inserter 10 attached to the implant. Again, because the inserter 10 is exclusively made of materials that are completely or mostly radiolucent, the inserter 10 allows the operator to visualize the implant and the surrounding hard and soft tissues so as to avoid critical anatomy without the need to disengage and reengage the inserter 10 from the implant.

In a preferred embodiment, the inserter 10 comprises high strength plastics such as PEEK™ (Polyetheretherketon) plastic available from Whitford Worldwide Company, Delaware, USA; carbon fiber; or thin aluminum. Tables I and II list some material properties of these types of materials.

TABLE I

Material properties of unidirectional carbon fiber and PEEK ™ plastic composite

| Property | Parallel to Fiber | Perpendicular to Fiber |
|---|---|---|
| Tensile strength (ksi) | 300 | 12.5 |
| Tensile modulus (msi) | 20 | 1.5 |
| Flexural strength (ksi) | 290 | 20 |
| Flexural modulus (msi) | 18.1 | 1.3 |
| Coefficient of thermal expansion (in./in./° F.) | $0.15 \times 10^{-6}$ | $17 \times 10^{-6}$ |

TABLE II

Material properties of PEEK ™ plastic composite and aluminum

| Property | Bidirectional Carbon Fiber/PEEK ™ (0°/90° direction) | Aluminum (2024-T3) |
|---|---|---|
| Density (lb/in.) | 0.056 | 0.100 |
| Flexural strength (ksi) | 1.37 | 67 |
| Flexural modulus (msi) | 7.7 | 10.5 |
| Specific strength (strength/density) | 2,446 | 670 |
| Specific modulus (modulus/density) | 137.5 | 105 |
| Thermal expansion, 70–300° F. (in./in./° F.) | $1.6 \times 10^{-6}$ | $14 \times 10^{-6}$ |
| Melting point (° F.) | 640 | 936 |

Moreover, the inserter 10 is adapted to firmly hold a spinal/orthopedic implant (not shown) such as a screw or a nail and to drive it accurately through bone under constant or occasional X-ray imaging. The geometry and mechanical function of the inserter 10 is dependent and may be customized to mate with the various implant geometries to achieve the above task.

If made of plastics, the inserter 10 may be adapted for a one time use (disposable) due to the toll of repeated hospital autoclaving (for sterilization) that may deteriorate most plastics. If the inserter 10 is made of carbon fibers and thin aluminum, then the inserter 10 may undergo many sterilization cycles without any or significant structural degradation, and still allow for good X-ray imaging, thereby allowing the inserter 10 to be reused.

Figure 2:
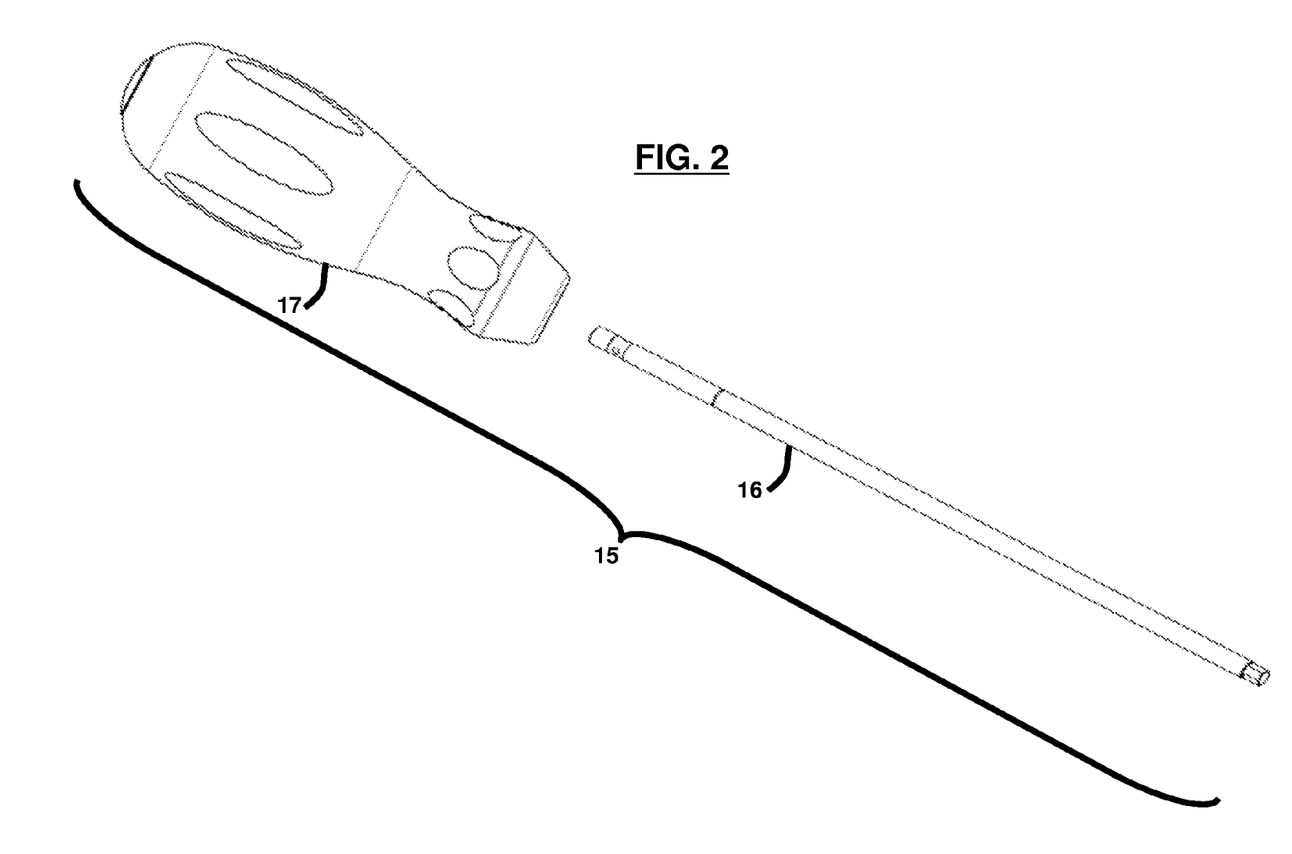
FIG. 2 illustrates a schematic diagram of a radiolucent inserter according to a second embodiment herein.

In an alternate embodiment, shown in FIG. 2, the inserter 15 may comprise a body portion 16 that operatively connects to a screwdriver handle 17. The screwdriver handle 17 may comprise any suitable configuration including the one illustrated in FIG. 2 or another configuration, such as the screwdriver handle described in U.S. patent application Ser. No. 11/076,670, filed on Mar. 10, 2005, the complete disclosure of which in its entirety is herein incorporated by reference.

Figure 3:
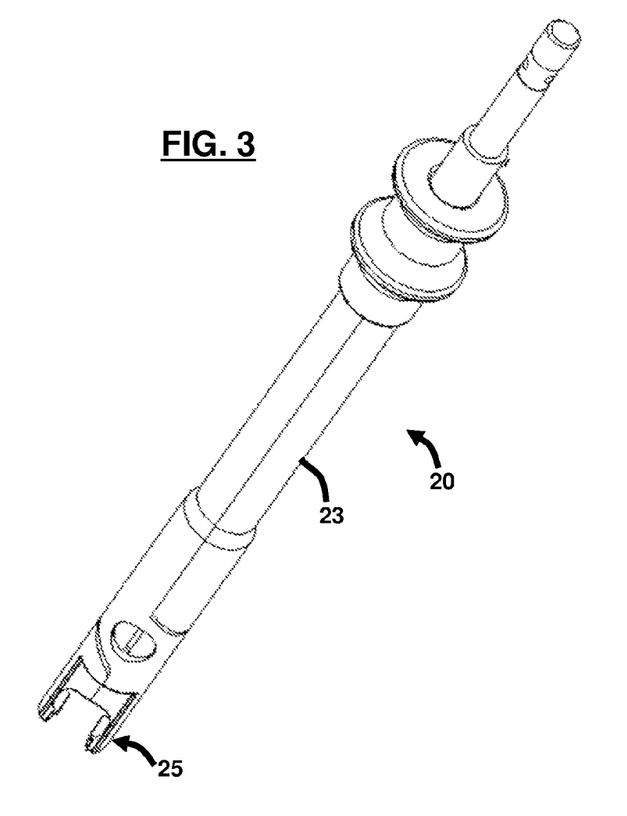
FIG. 3 illustrates a schematic diagram of a radiolucent inserter according to a third embodiment herein.

In another alternate embodiment, shown in FIG. 3, the inserter 20 may comprise a body portion 23 comprising predominantly radiolucent material and a small driving tip 25 comprising hard steel, wherein the tip 25 is dimensioned and configured of such a small mass and profile that it will not interfere with the desired imaging capability during surgery.

Figure 4:
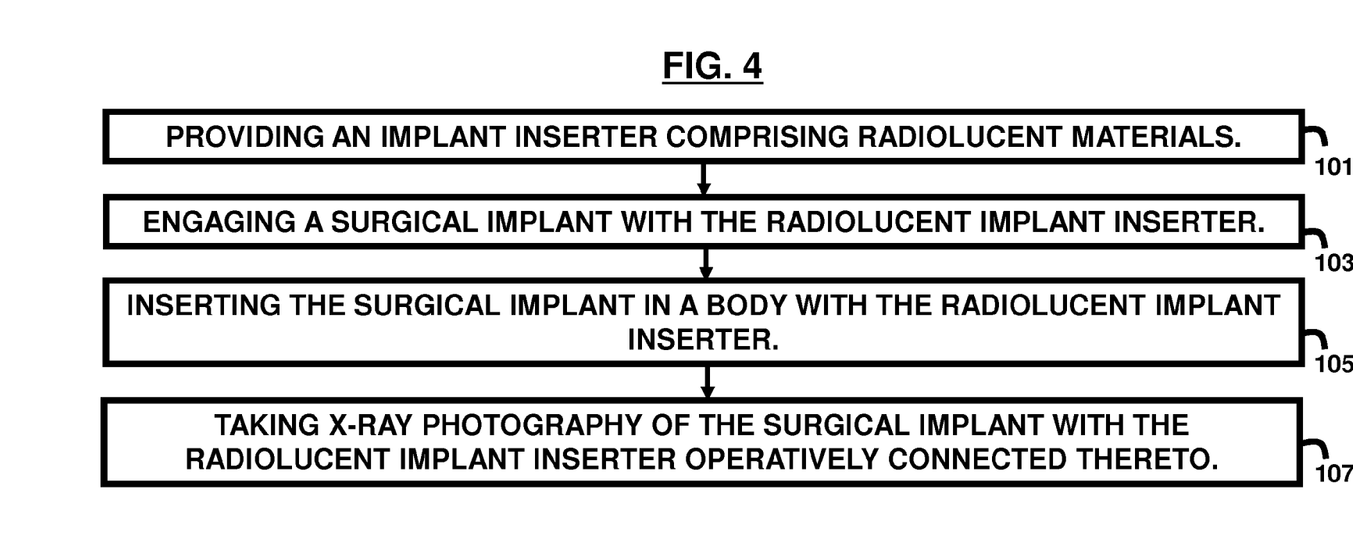
FIG. 4 is a flow diagram illustrating a preferred method according to an embodiment herein.

FIG. 4, with reference to FIGS. 1 through 3, is a flow diagram illustrating a method of performing a surgical procedure according to an embodiment herein, wherein the method comprises providing (101) an implant inserter 10, 15, 20 comprising radiolucent materials; engaging (103) a surgical implant (not shown) with the radiolucent implant inserter 10, 15, 20; inserting (105) the surgical implant in a body (not shown) (such as a human spine) with the radiolucent implant inserter 10, 15, 20; and taking (107) X-ray photography of the surgical implant with the radiolucent implant inserter 10, 15, 20 operatively connected thereto, wherein the radiolucent implant inserter 10, 15, 20 is at least partially within the body during the taking of the X-ray photography. Preferably, the implant inserter 10, 15, 20 comprises a body portion 13, 16, 23 comprising the radiolucent materials; and a tip portion 14, 25 operatively connected to the tip portion. In one embodiment the tip portion 14 comprises radiolucent materials. In another embodiment the tip portion 25 comprises steel. Preferably, the radiolucent materials comprise any of plastic carbon fibers, and thin aluminum. Furthermore, the implant inserter 10, 15, 20 preferably comprises a torque capacity of at least 6 Nm. Also, the implant inserter 10, 15, 20 may comprise a screwdriver. Additionally, the method may further comprise disposing the implant inserter 10, 15, 20 after use.

FIGS. 5(A) through 5(D) illustrate an attachment mechanism 109 according to one embodiment herein. Generally, the attachment mechanism 109 generally comprises a first arm 160, a second arm 170, and a locking sleeve 111. According to one embodiment herein, the attachment mechanism 109 is adapted to attach to a handle (such as the screwdriver handle described in U.S. patent application Ser. No. 11/076,670, filed on Mar. 10, 2005, the complete disclosure of which in its entirety is herein incorporated by reference), but can be removed if necessary.

Figure 5A:
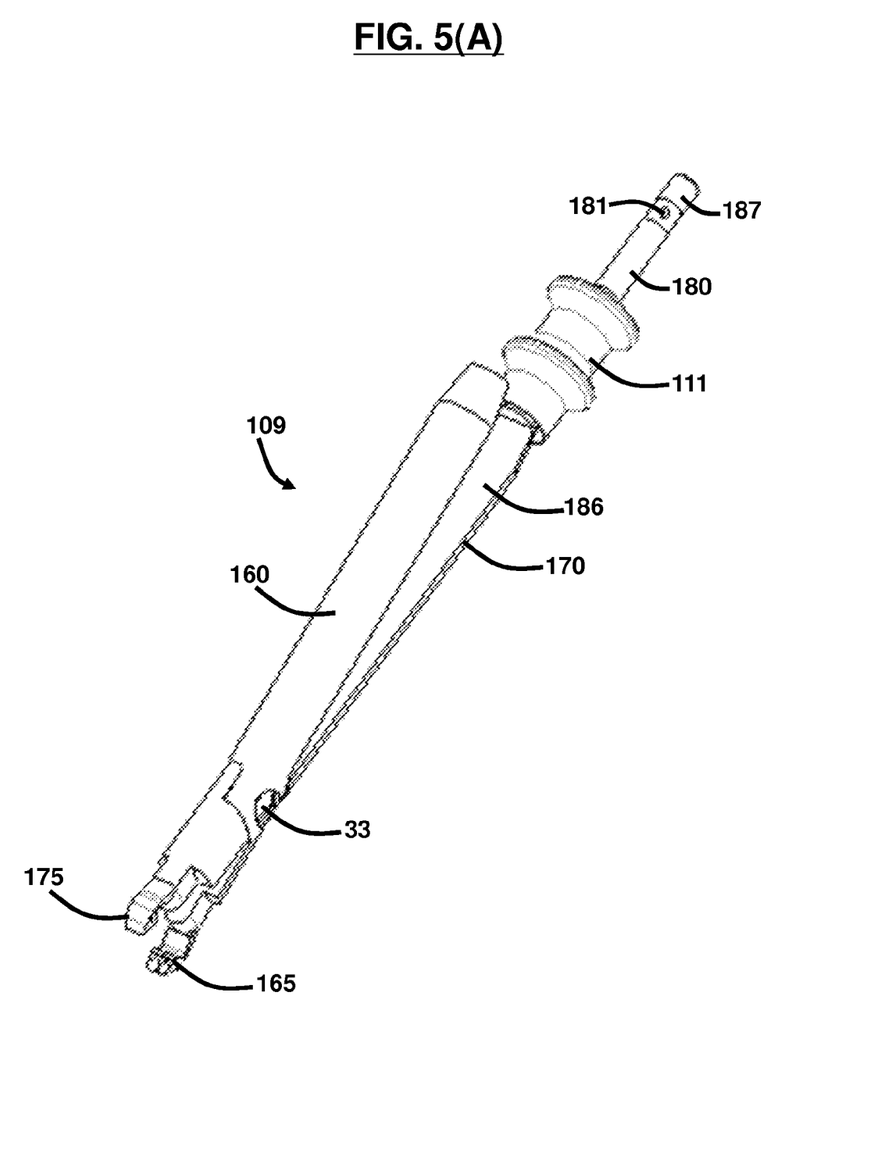
FIGS. 5(A) through 5(D) illustrate various views of an attachment mechanism according to the embodiments herein.
Figure 5B:
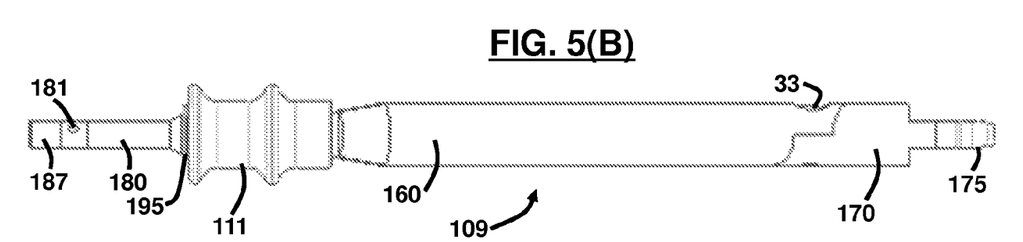
Figure 5C:
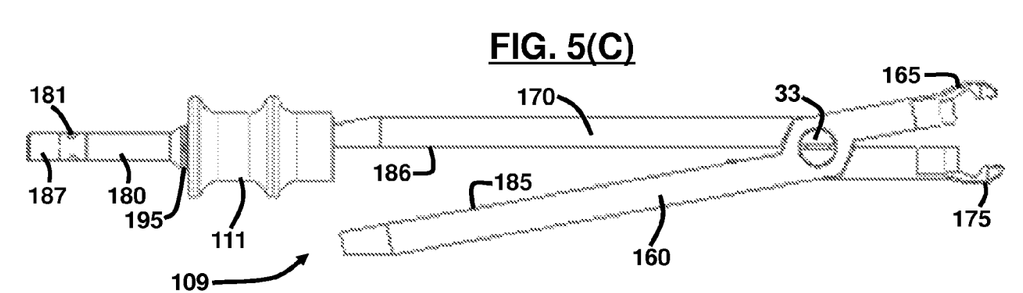
Figure 5D:
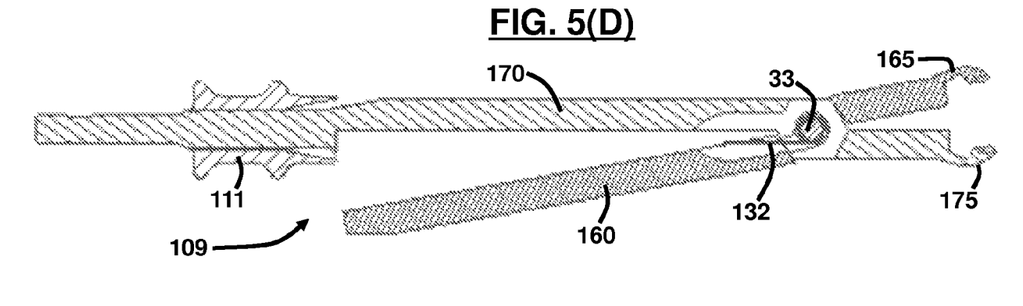
Figure 6A:
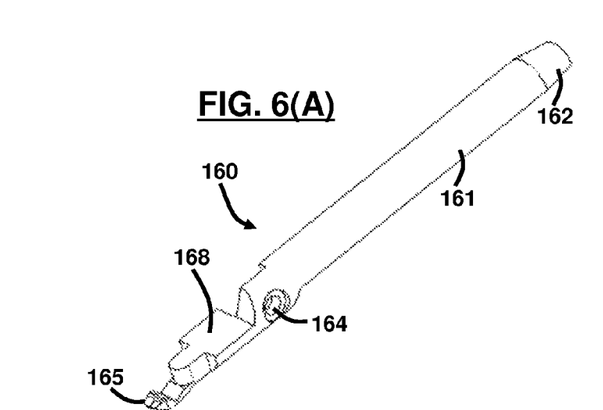
Figure 6B:
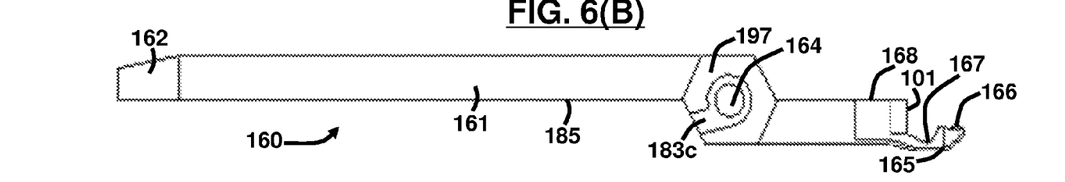
Figure 6C:
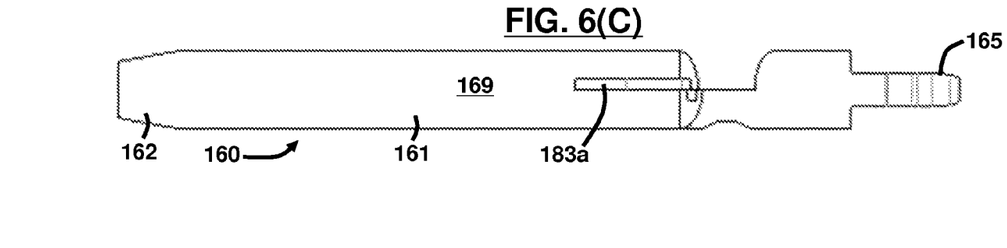

The first arm 160 of the attachment mechanism 109 of FIGS. 5(A) through 5(D) is further depicted in FIGS. 6(A) through 6(C) (with reference to FIGS. 5(A) through 5(D)). The first arm 160 generally comprises a shaft portion 161 having a tapered end 162 and a prong end 165 opposite to the tapered end 162. Preferably, a hexagonally-shaped linking portion 197 joins the shaft portion 161 to the prong end 165. A lateral slot 183a circular slot 183c, which connect to one another, are configured in the linking portion 197 and in the shaft portion 161 located near the linking portion 197. Moreover, the shaft portion 161 further includes a generally curved outer wall surface 169 and a generally flat inner wall surface 185. The linking portion 197 also includes a hole 164 configured through the entire thickness of the linking portion 197. Preferably, the hole 164 has threads (not shown) circumferentially configured around the outer periphery of the hole 164. Furthermore, a generally flat alignment portion 168 is configured between the prong end 165 and the linking portion 197. The prong end 165 further includes a prong tip 166 configured at the free end of the prong end 165, an indent portion 167 configured between the prong tip 166 and the alignment portion 168, and a driving wall 101 configured at the edge of the alignment portion 168.

Figure 7A:
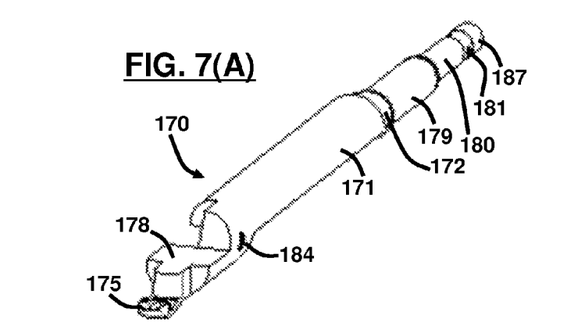
Figure 7B:
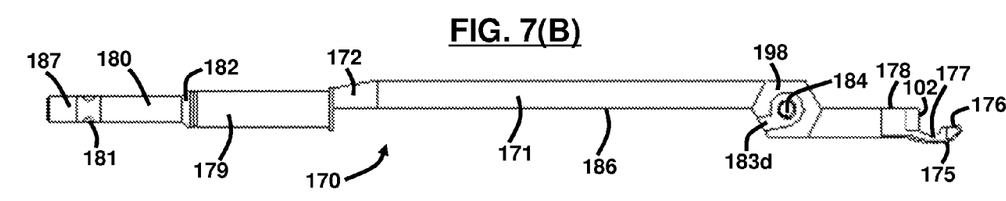
Figure 7C:
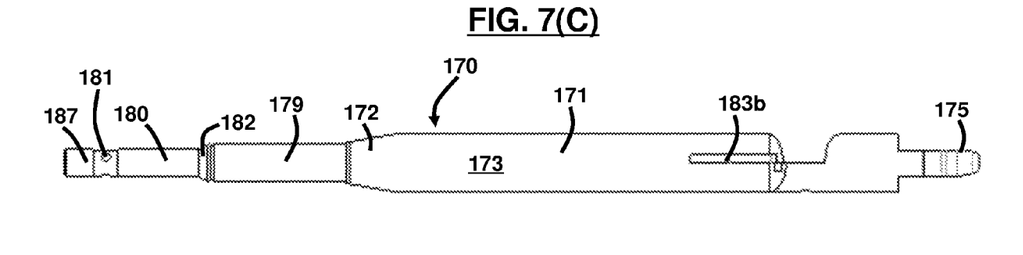

The second arm 170 of the attachment mechanism 109 of FIGS. 5(A) through 5(D) is further depicted in FIGS. 7(A) through 7(C) (with reference to FIGS. 5(A) through 6(C)). The second arm 170 generally comprises a shaft portion 171 having a prong end 175. Preferably, a hexagonally-shaped linking portion 198 joins the shaft portion 171 to the prong end 175. A lateral slot 183b and a circular slot 183d, which connect to one another, are configured in the linking portion 198 and in the shaft portion 171 located near the linking portion 198. Moreover, the shaft portion 171 further includes a generally curved outer wall surface 173 and a generally flat inner wall surface 186. Additionally, a hole 184 is configured through the entire thickness of the linking portion 198 and dimensioned similarly to the hole 164 of the linking portion 197 of the first arm 160. Preferably, the hole 184 has threads (not shown) circumferentially configured around the outer periphery of the hole 184. Furthermore, a generally flat alignment portion 178 is configured between the prong end 175 and the linking portion 198. The prong end 175 further includes a prong tip 176 configured at the free end of the prong end 175, an indent portion 177 configured between the prong tip 176 and the alignment portion 178, and a driving wall 102 configured at the edge of the alignment portion 168.

The shaft portion 171 is adjacent to a tapered section 172, which has a thickness similar to the thickness of the shaft portion 171. Adjacent to the tapered section 172 is a fully cylindrical first handle attachment shaft 179, which connects to a smaller tapered section 182, which then connects to a second handle attachment shaft 180, which has a hole 181 disposed through an entire thickness therein. Preferably, the second handle attachment shaft 180 is dimensioned slightly smaller than the first handle attachment shaft 181 and is also in a cylindrical configuration. A tip 187, which is diametrically dimensioned similarly to the second handle attachment shaft 180, is configured next to the second handle attachment shaft 180 and is positioned at an opposite end to the prong end 175 of the second arm 170.

Figure 8A:
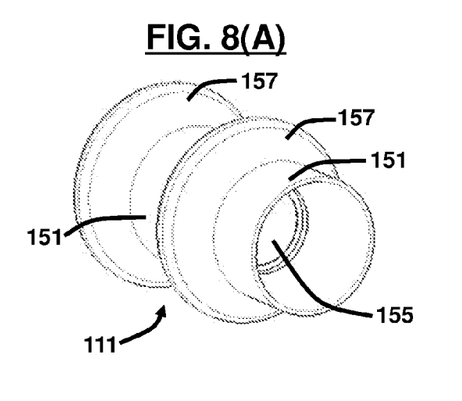
Figure 8B:
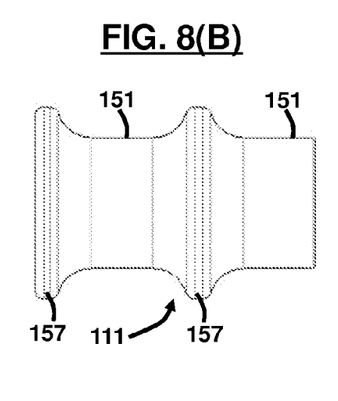
Figure 8C:
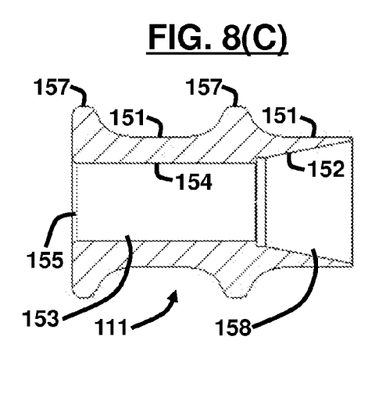
Figure 9:
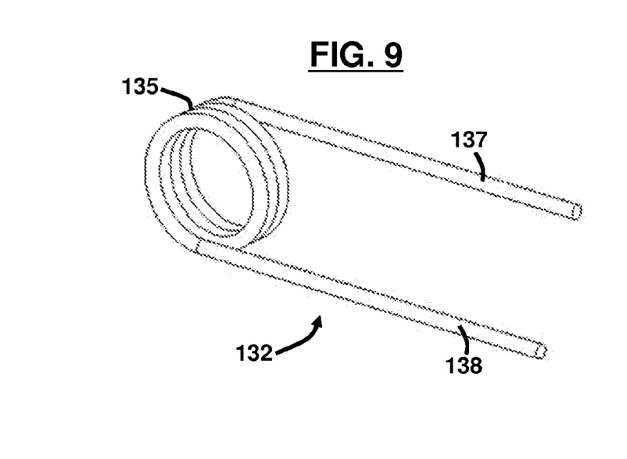
FIG. 9 illustrates the torsion spring of the attachment mechanism of FIGS. 5(A) through 5(D) according to the embodiments herein.
Figure 10:
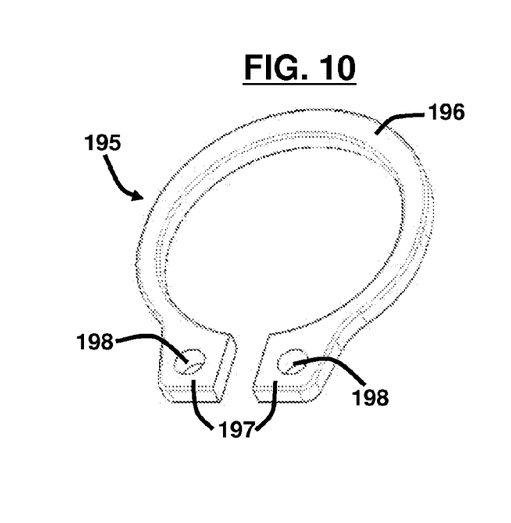
FIG. 10 illustrates the retaining clip of the attachment mechanism of FIGS. 5(A) through 5(D) according to the embodiments herein.

The locking sleeve 111 of FIGS. 5(A) through 5(D) is further shown in FIGS. 8(A) through 8(C). Generally, the locking sleeve 111 comprises a tubular structure 151 having a plurality of spaced apart circular flanges 157 configured around the tubular structure 151. The tubular structure 151 has a hollow inner portion 155 and has a cylindrical portion 153 having a generally cylindrical inner surface 154. Additionally, the tubular structure 151 has a tapered end 158 having a generally tapered inner surface 152. The torsion spring 132 of FIG. 5(D) is shown with more particularity in FIG. 9. The torsion spring 132 comprises a coiled central portion 135 and a pair of elongated ends 137, 138 distally located from the coiled central portion 135. The retaining clip 195 of FIGS. 5(B) and 5(C) is further shown in FIG. 10. The retaining clip 195 may be formed in any appropriate configuration. For example, the retaining clip 195 may be formed in a generally circular ring-like configuration comprising a ring-like body portion 196 terminating in a pair of end portions 197, wherein the end portions 197 each comprise a hole 198. As shown in the example in FIG. 10, the end portions 197 are separate from one another.

Most medical device manufacturers prefer using purely metal or mostly metal in tools they manufacture for surgeons. The predominant reason behind this motive is the durability of metal products and tools especially in repetitive use environments such as a hospital setting whereby tools undergo extensive sterilization processes and are handled, in some cases, on a daily basis. Therefore, prior to the development of the inserter 10, 15, 20 provided by the embodiments herein, medical device manufacturers have been largely unwilling to develop non-metal tools because their customers (i.e., hospitals and surgeons) have requested that their surgical instruments meet certain specifications, mostly that their tools comprise high strength metal materials. Accordingly, the industry would generally find the inserter 10, 15, 20 provided by the embodiments herein to be unconventional and clearly an unexpected advancement in the art given the benefits it affords. Moreover, the inserter 10, 15, 20 is capable of providing the torque required for inserting a screw, which is approximately 5-6 Nm.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A surgical inserter comprising:
   a handle comprising:
      a base portion; and
      a locking sleeve mounted on said base portion;
   a body portion operatively connected to said handle, said body portion comprising:

a plurality of arms pivotally attached to one another, wherein each arm comprises a substantially semi-circular bifurcated wall having a substantially flat surface with a prong outwardly extending from a middle portion of said wall, wherein each said prong comprises a fixed tip portion operatively connected to each arm of said body portion and extending from a block portion comprising a tapered end connecting to planar side surfaces, wherein when said plurality of arms are squeezed together, the arms form a substantially cylindrical shape such that an outer lateral edge of each said prong extends beyond a width defined by a diameter of said cylindrical shape, and wherein a width of an entirety of said block portion is approximately half of said width defined by said diameter of said cylindrical shape; and a bias element mounted in at least one of said plurality of arms, wherein said body portion consists of radiolucent materials and said locking sleeve is slidably mounted around at least one of said plurality of arms.

2. The inserter of claim 1, wherein said tip portion comprises radiolucent materials.

3. The inserter of claim 1, wherein said tip portion comprises steel.

4. The inserter of claim 1, wherein said tip portion engages a surgical implant.

5. The inserter of claim 2, wherein said radiolucent materials comprise any of plastic, carbon fibers, and aluminum.

6. The inserter of claim 1, wherein said tip portion comprises a torque capacity of at least 6 Nm.

7. The inserter of claim 1, wherein said body portion is dimensioned and configured as a screwdriver.

8. A surgical instrument, comprising:
a handle comprising:
a base portion; and
a locking sleeve mounted on said base portion;
means for inserting an orthopedic implant into a human body, wherein said orthopedic implant comprises radiopaque materials; and
a body portion coupled to said handle and said means for inserting an orthopedic implant, said body portion comprising:
a plurality of arms pivotally attached to one another, wherein each arm comprises a substantially semi-circular bifurcated wall having a substantially flat surface with a prong outwardly extending from a middle portion of said wall, wherein each said prong comprises a gripping portion extending from a block portion comprising a tapered end connecting to planar side surfaces, wherein when said plurality of arms are squeezed together, the arms form a substantially cylindrical shape such that an outer lateral edge of each said prong extends beyond a width defined by a diameter of said cylindrical shape, and wherein a width of an entirety of said block portion is approximately half of said width defined by said diameter of said cylindrical shape;
a bias element mounted in at least one of said plurality of arms,
wherein said body portion consists of radiolucent materials, and
said locking sleeve is slidably mounted around at least one of said plurality of arms.

9. The surgical instrument of claim 8, wherein said means for inserting an orthopedic implant consists of radiopaque materials.

10. The surgical instrument of claim 8, wherein said means for inserting an orthopedic implant consists of radiolucent materials.

11. The surgical instrument of claim 8, wherein said orthopedic implant comprises at least one of a nail and a screw.

12. The surgical instrument of claim 8, further comprising means for driving said orthopedic implant through bone.

13. The surgical instrument of claim 12, wherein said means for driving said orthopedic implant through bone comprises radiolucent materials.

14. The surgical instrument of claim 13, wherein said means for driving said orthopedic implant through bone further comprises a screwdriver tip that structurally mates with said orthopedic implant.

\* \* \* \* \*

UNITED STATES PATENT AND TRADEMARK OFFICE
CERTIFICATE OF CORRECTION

| | | |
|---|---|---|
| PATENT NO. | : 7,981,116 B2 | |
| APPLICATION NO. | : 11/753632 | |
| DATED | : July 19, 2011 | |
| INVENTOR(S) | : Ralph F. Reeder, Jr. et al. | |

It is certified that error appears in the above-identified patent and that said Letters Patent is hereby corrected as shown below:

Column 2, line 43, please delete "6(D)" and in its place, please insert --6(C)--.

Column 2, line 46, please delete "7(D)" and in its place, please insert --7(C)--.

Column 3, line 49, please delete "8(D)" and in its place, please insert --8(C)--.

Signed and Sealed this
Thirtieth Day of August, 2011

David J. Kappos
*Director of the United States Patent and Trademark Office*